(12) United States Patent
Lynn

(10) Patent No.: US 11,098,910 B1
(45) Date of Patent: Aug. 24, 2021

(54) HVAC DECONTAMINATION SYSTEM WITH REGULATED OZONE OUTPUT BASED ON MONITORED OZONE LEVEL IN AMBIENT AIR

(71) Applicant: Daniel W. Lynn, Omaha, NE (US)

(72) Inventor: Daniel W. Lynn, Omaha, NE (US)

( * ) Notice: Subject to any disclaimer, the term of this patent is extended or adjusted under 35 U.S.C. 154(b) by 0 days.

(21) Appl. No.: 17/325,966

(22) Filed: May 20, 2021

Related U.S. Application Data

(63) Continuation-in-part of application No. 17/200,799, filed on Mar. 13, 2021, now Pat. No. 11,045,571.

(51) Int. Cl.
| | |
|---|---|
| *A61L 9/12* | (2006.01) |
| *F24F 8/40* | (2021.01) |
| *F24F 13/04* | (2006.01) |
| *F24F 8/60* | (2021.01) |
| *A61L 9/015* | (2006.01) |
| *F24F 110/74* | (2018.01) |

(52) U.S. Cl.
CPC ............... *F24F 8/40* (2021.01); *A61L 9/015* (2013.01); *A61L 9/122* (2013.01); *F24F 8/60* (2021.01); *F24F 13/04* (2013.01); *F24F 2110/74* (2018.01)

(58) Field of Classification Search
CPC ............. A61L 9/12; A61L 9/122; A61L 9/015
See application file for complete search history.

(56) References Cited

U.S. PATENT DOCUMENTS

| | | |
|---|---|---|
| 1,363,589 A | 12/1920 | Hartman |
| 6,153,105 A | 11/2000 | Tadlock et al. |
| 6,334,328 B1 | 1/2002 | Brill |
| 6,685,825 B1 | 2/2004 | Chang |
| 6,994,832 B2 * | 2/2006 | Borgstrom .............. C01B 13/11 422/186.07 |
| 8,071,526 B2 | 12/2011 | Lynn |
| 8,075,705 B2 | 12/2011 | Lynn |
| 9,068,149 B2 | 6/2015 | Lynn |
| 9,151,528 B2 | 10/2015 | Erbs et al. |
| 9,174,845 B2 | 11/2015 | Lynn |
| 9,522,348 B2 | 12/2016 | Lynn |
| 10,314,932 B2 | 6/2019 | Huang |
| 10,426,855 B2 | 10/2019 | Lynn |
| 10,823,438 B1 | 11/2020 | Baumgartner et al. |
| 2003/0156978 A1 | 8/2003 | Gillette |
| 2004/0004042 A1 | 1/2004 | Hadley et al. |
| 2004/0168989 A1 | 9/2004 | Tempest |
| 2004/0262241 A1* | 12/2004 | Socha ................ B01D 53/8675 210/760 |
| 2009/0142225 A1 | 6/2009 | Tornqvist |
| 2009/0185959 A1 | 7/2009 | Weber et al. |
| 2010/0219137 A1 | 9/2010 | Lacasse |
| 2011/0165018 A1 | 7/2011 | Lynn |

(Continued)

*Primary Examiner* — Robert A Hopkins
(74) *Attorney, Agent, or Firm* — Nasr Patent Law LLC; Faisal K. Abou-Nasr

(57) ABSTRACT

An HVAC decontamination system with regulated ozone output based on monitored ozone level in ambient air is disclosed. The HVAC decontamination system includes an ozone supply unit and an air analyzer. Based on one or more control signals from the air analyzer, the ozone supply unit is configured to: (i) generate ozone when an amount of ozone per unit volume of air is less than a predetermined threshold; and (ii) cease to generate ozone when the amount of ozone per unit volume of air exceeds the predetermined threshold.

18 Claims, 3 Drawing Sheets

(56) References Cited

U.S. PATENT DOCUMENTS

| | | |
|---|---|---|
| 2013/0193081 A1 | 8/2013 | Vasiliu et al. |
| 2013/0341285 A1 | 12/2013 | Marion |
| 2014/0027388 A1 | 1/2014 | Constant |
| 2014/0263097 A1 | 9/2014 | Lynn |
| 2016/0251243 A1 | 9/2016 | Lynn |

* cited by examiner

HVAC DECONTAMINATION SYSTEM WITH REGULATED OZONE OUTPUT BASED ON MONITORED OZONE LEVEL IN AMBIENT AIR

CROSS-REFERENCE TO RELATED APPLICATIONS

The present application is a Continuation-in-Part of U.S. application Ser. No. 17/200,799 filed Mar. 13, 2021 and titled "REDUCED NOISE AIR DECONTAMINATOR," which is incorporated herein by reference.

TECHNICAL FIELD

The present disclosure relates to systems for improving air quality, and more particularly, to an HVAC decontamination system.

BACKGROUND

Odors may arise from the decomposition products of meat or fish protein, containing sulfur, nitrogen, and oxygen, as well as spoilage microorganisms that belong to four major groups: bacteria, viruses, protozoa, or fungi. Odors can also arise from fires, (incomplete combustion), fats, chemicals, etc. The smells that humans react to most strongly are associated with food odor sensations which are often the result of a complex interaction of many, sometimes hundreds, of chemical compounds on the sensory organs of the nose. The smell in a modern office building is a "cocktail" made up of the smells of more than a thousand substances (sweat, tobacco, carpeting, cleansers, plants, ink, etc.).

The total smell perceived is often different from, and sometimes stronger than, the sum of its parts. Bad smells can cause health effects, such as headache, nausea, and sleeplessness. Bad odor compounds are generally not poisonous, at least not in the concentrations at which they begin to cause an odor nuisance. If the concentration of an odor in air is below levels of irritation (levels known to cause eye, nose, or throat irritation in people), the symptoms will pass when you move out of the exposure area. However, if the concentration of an odor in air is at or above levels of irritation and the exposure duration is longer, the symptoms may last after moving out of the exposure area.

Circulated air may also become infected with pathogens (e.g., bacteria, viruses, etc.), resulting in transmission of infectious diseases within an air-conditioned environment. At high enough concentrations, pathogens in circulated air can pose a serious health risk to occupants of an air-conditioned environment (e.g., a hotel, restaurant, grocery store, department store, office building, single/multi-family residential building, hospital, school, arena, concert/event hall, airplane cabin, bus, train, etc.).

To effectively prevent symptoms from unpleasant odors and provide a clean and safe environment, there is a need for systems that can safely deodorize and disinfect air being circulated throughout an air-conditioned environment.

Many types of devices have been previously provided to reduce odors in indoor areas such as restaurant kitchens, bathrooms, grocery stores, classrooms, school locker rooms, office buildings, homes, veterinary clinics, hospitals, hotels, etc. However, most existing devices utilize chemicals or masking deodorizers. Further, the existing deodorizing devices are typically unable to disinfect air and contact surfaces while deodorizing the area in which the existing deodorizing devices are placed. The existing deodorizing devices are also limited in their ability to treat bacteria, viruses, mildew, molds, allergens, smoke odors, or food preparation odors.

Common inorganic agents, such as sodium hypochlorite, hydrogen peroxide, and potassium permanganate can readily oxidize most of the usual odor compounds. In general, the cheapest of these is sodium hypochlorite (chlorine bleach). The extent of poisoning caused by chlorine depends on the amount of chlorine a person is exposed to, how the person was exposed, and the length of time of the exposure. When chlorine gas comes into contact with moist tissues, such as the eyes, throat, and lungs, an acid is produced that can damage these tissues. Industrially, hydrogen peroxide has been used for years to deodorize, disinfect, and neutralize hazardous pollutants.

Ozone is also a very powerful oxidizing agent and is safe for humans when the time and amount of exposure is controlled. Ozone in water decomposes to oxygen and hydroxyl radicals, each of which has a higher oxidation potential than either ozone or chlorine. The activity of hydroxyl radical is enhanced by a higher pH. Ozone can oxidize odorous organic and inorganic compounds in the presence of water. Also, in the presence of moisture, it is a powerful germicide. Ozone can also directly oxidize odorous compounds by attacking double bonds or a reactive site. Thus, ozone may be used to reduce odors and disinfect air/surfaces without the current limitations of existing deodorizing and/or disinfecting devices.

SUMMARY

Aspects of this disclosure are directed to an HVAC decontamination system with regulated ozone output based on monitored ozone level in ambient air.

In embodiments, the HVAC decontamination system includes an ozone supply unit and an air analyzer.

The ozone supply unit includes an enclosure having one or more air intake ports and one or more ozone output ports. A plurality of ozone generators are disposed within the supply unit enclosure. The ozone generators are fluidically coupled to the one or more air intake ports and the one or more ozone output ports of the supply unit enclosure. One or more controllers are also disposed within the supply unit enclosure. The one or more controllers are communicatively coupled to the plurality of ozone generators.

The air analyzer is configured to monitor an amount of ozone per unit volume of air using an ozone sensor disposed at a selected location within an air-conditioned environment (e.g., at or near a supply vent or a blower output). The air analyzer is further configured to transmit one or more control signals based on the amount of ozone per unit volume of air to the one or more controllers of the ozone supply unit, where the one or more controllers are configured to: (i) cause the plurality of ozone generators to generate ozone when the amount of ozone per unit volume of air is less than a predetermined threshold; and (ii) cause the plurality of ozone generators to cease to generate ozone when the amount of ozone per unit volume of air exceeds the predetermined threshold.

In some embodiments, one or more tubes are coupled to the one or more ozone output ports of the supply unit enclosure and are configured to deliver the ozone generated by the ozone generators to an air return duct of a HVAC system. The ozone may then flow through the air return duct into an air handler configured to condition the air received via the air return duct. The air handler may help to evenly mix/diffuse the ozone into the air by circulating and/or blowing the air within one or more chambers or ducts. The air handler may be configured to output the conditioned air (containing ozone) into a supply duct that delivers conditioned air from the air handler to one or more supply vents. The one or more supply vents are configured to output the conditioned air into the air-conditioned environment.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

Reference will now be made in detail to the subject matter disclosed, which is illustrated in the accompanying drawings.

Embodiments of this disclosure are directed to an HVAC decontamination system for disinfecting air and HVAC systems with ozone ($O_3$) gas. Ozone is a powerful oxidizing agent that is safe for humans as long as the amount of ozone per unit volume of air is kept within a certain range (e.g., 0.01 to 0.3 ppm, or more particularly 0.05 to 0.2 ppm). At higher concentrations, it may be necessary to control a length of time that humans/animals are exposed and/or type of activity taking place in the ozone-enriched environment. For example, OSHA guidelines for ozone in the workplace are as follows: 0.2 ppm for no more than 2 hours exposure; 0.1 ppm for 8 hours per day exposure doing light work; 0.08 ppm for 8 hours per day exposure doing moderate work; and 0.05 ppm for 8 hours per day exposure doing heavy work.

Ozone in water decomposes to oxygen and hydroxyl radicals, each of which has a higher oxidation potential than either ozone or chlorine. The activity of hydroxyl radical is enhanced by a higher pH. Ozone can oxidize odorous organic and inorganic compounds in the presence of water. Also, in the presence of moisture, it is a powerful germicide. Ozone can also directly oxidize odorous compounds by attacking double bonds or a reactive site. Thus, ozone may be used to reduce odors and disinfect air/surfaces without the current limitations of existing deodorizing and/or disinfecting devices. The amount of ozone required may depend on the odor levels being controlled and operational safety parameters (e.g., occupancy, exposure time, types of activity, etc.) of an environment (e.g., a hotel, restaurant, grocery store, department store, office building, single/multi-family residential building, hospital, school, arena, concert/event hall, airplane cabin, bus, train, etc.).

Figure 1:
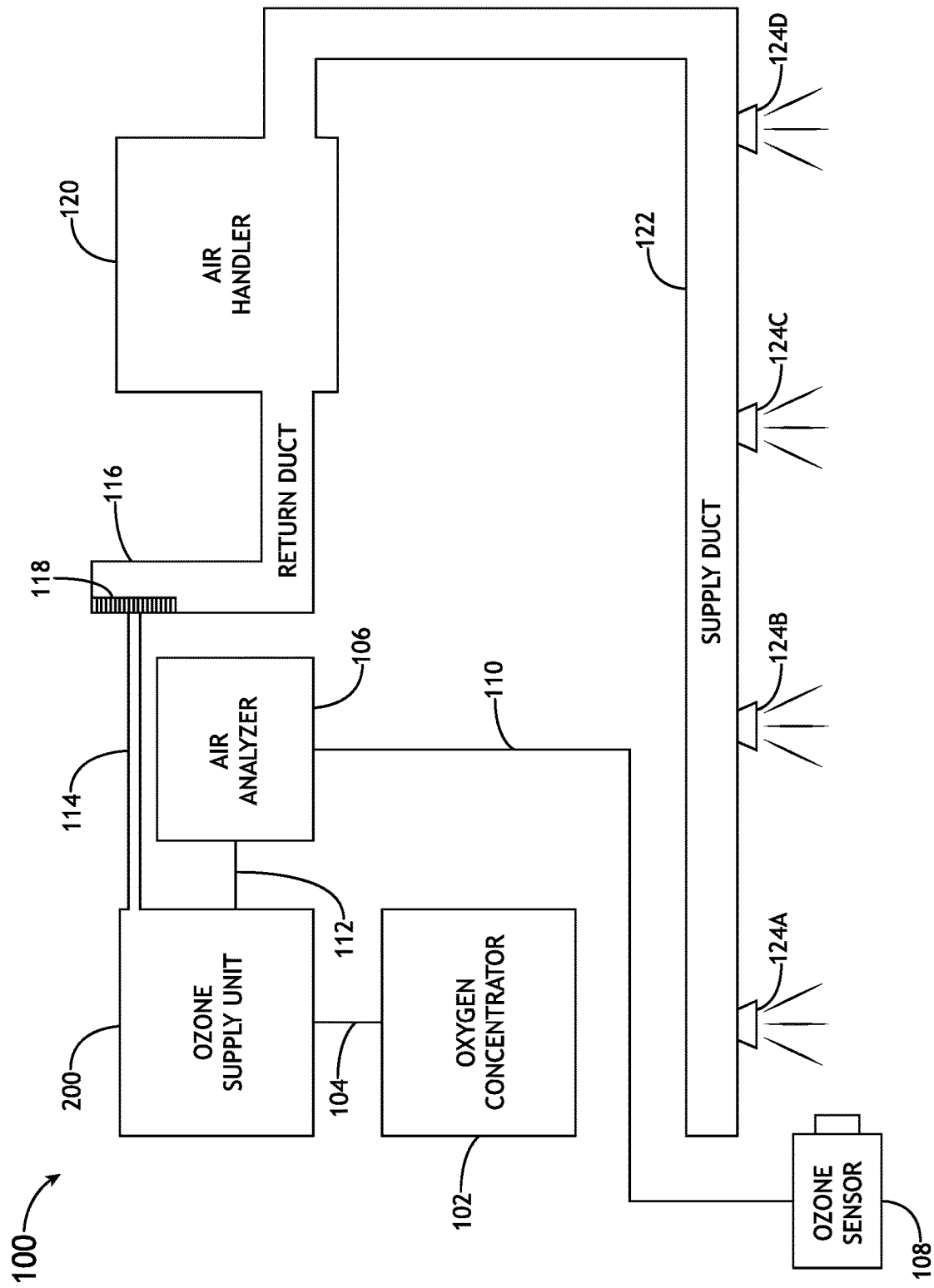
FIG. 1 is block diagram illustrating an HVAC decontamination system with regulated ozone output based on monitored ozone level in ambient air, in accordance with one or more embodiments of this disclosure.
Figure 2:
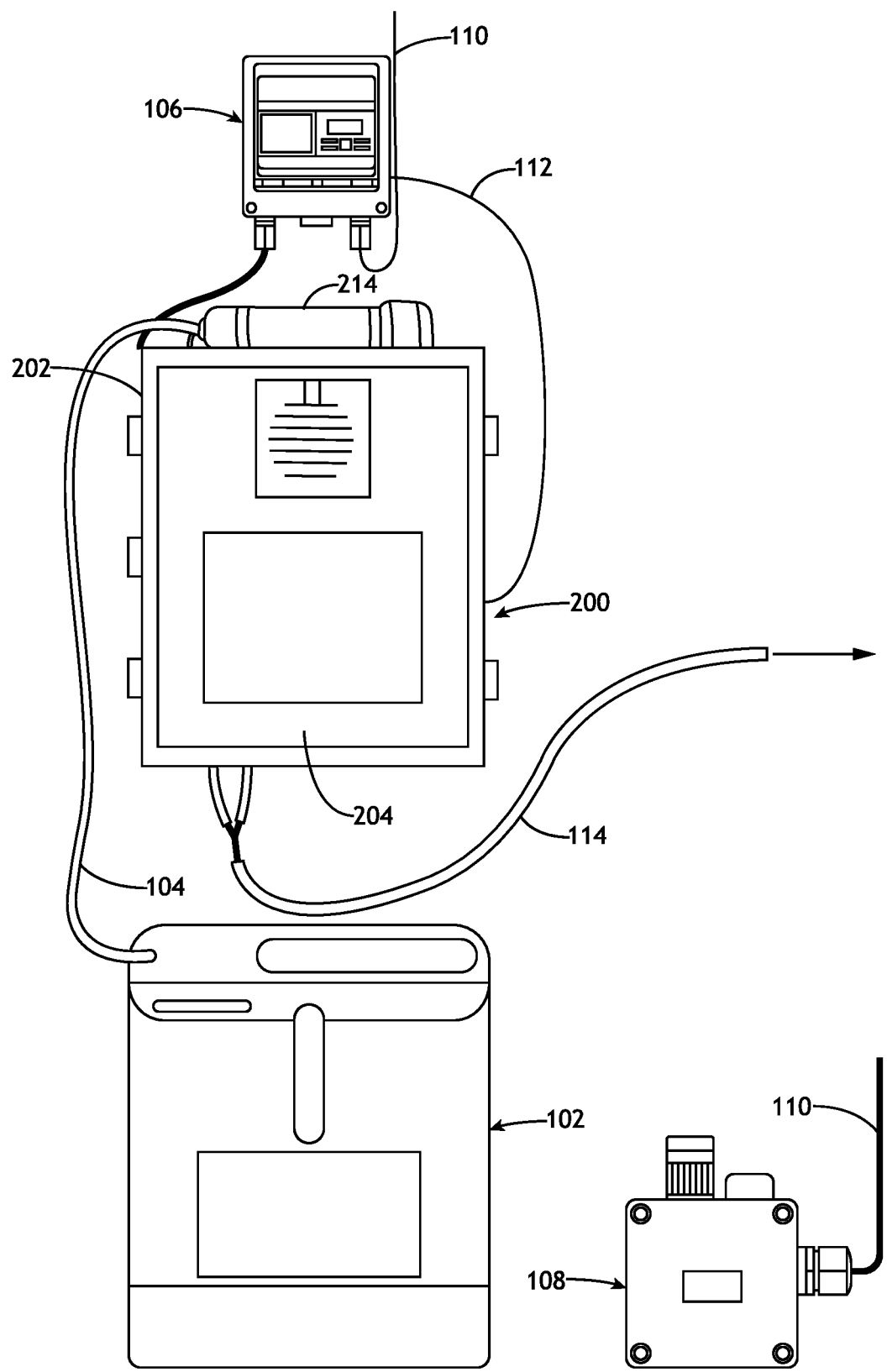
FIG. 2 is a front view of an ozone concentrator, an ozone supply unit, an air analyzer, and an ozone sensor of the HVAC decontamination system illustrated in FIG. 1, in accordance with one or more embodiments of this disclosure.
Figure 3:
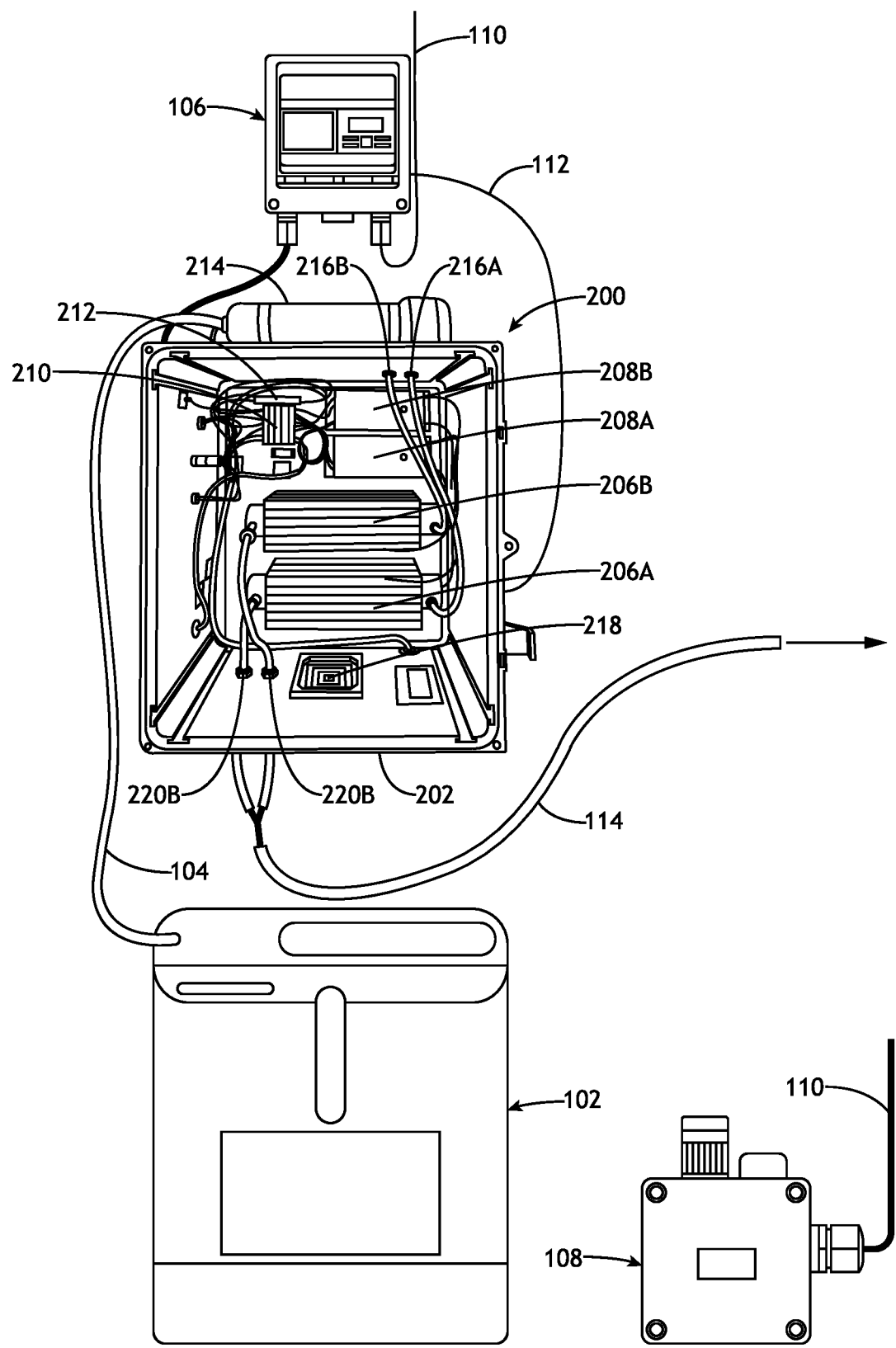
FIG. 3 is a front view of the ozone concentrator, the ozone supply unit, the air analyzer, and the ozone sensor of FIG. 2, wherein the ozone supply unit is open/uncovered, in accordance with one or more embodiments of this disclosure.

FIGS. 1 through 3 illustrate an HVAC decontamination system 100 for disinfecting air and HVAC systems with ozone gas, in accordance with one or more embodiments of this disclosure. The HVAC decontamination system 100 includes an ozone supply unit 200 and an air analyzer 106.

As shown in FIG. 2, the ozone supply unit 200 may include a supply unit enclosure 202. In embodiments, the supply unit enclosure 202 and the air analyzer 106 are independently locatable, separate structures. While the supply unit enclosures 202 and the air analyzer 106 are separate and capable of being disposed at a distance from one another, the supply unit enclosures 202 and the air analyzer 106 may be communicatively coupled by one or more connectors 112 (e.g., wires, cables, optical fibers, etc.) for transmitting signals between the ozone supply unit 200 and the air analyzer 106. In other embodiments, the ozone supply unit 200 and the air analyzer 106 may include wireless communication interfaces (e.g., wireless receivers, transmitters, and/or transceivers) for sending signals from one device to the other.

The supply unit enclosure 202 may have a securable lid/cover 204 that can enclose (e.g., when secured/closed) and provide access to (e.g., when removed/opened) the components housed in an interior portion of the supply unit enclosure 202. As shown in FIG. 2, the securable lid/cover 204 may be secured to the supply unit enclosure 202 by a hinge on one side and a latch or fastener on an opposing side. In other embodiments, the securable lid/cover 204 may be secured to the supply unit enclosure 202 by one or more fasteners (e.g., screws to mate with bores in the supply unit enclosure 202, latches, interference fit fasteners, clipping fasteners, magnetic fasteners, or the like). The supply unit enclosure 202 may further include coupling portions to couple with a power source, a switch to engage or disengage power to the ozone supply unit 200/system 100, an indicator (e.g., a light source), any combination thereof, and so forth.

FIG. 3 illustrates the ozone supply unit 200 with the lid/cover 204 removed from the supply unit enclosure 202, in accordance with one or more embodiments of this disclosure. As shown in FIG. 2, the supply unit enclosure 202 includes one or more air intake ports 216 (e.g., ports 216A and 216B) and one or more ozone output ports 220 (e.g., ports 220A and 220B). The ozone supply unit 200 includes a plurality of ozone generators 206 (e.g., generators 206A and 206B) disposed within the supply unit enclosure 202. The ozone generators 206 are fluidically coupled to the one or more air intake ports 216 and the one or more ozone output ports 220 of the supply unit enclosure 202. One or more controllers 208 (e.g., controllers 208A and 208B) are also disposed within the supply unit enclosure 202. The one or more controllers 208 are communicatively coupled to the ozone generators 206.

In embodiments, each of the ozone generators 206 may include a corona discharge tube configured to use oxygen supplied via the one or more air intake ports 216 to generate ozone, such as through splitting of oxygen molecules in the air through electrical discharge caused by supplying power to a dielectric material within the corona discharge tube. For example, each ozone generator 206 may include an input port that is fluidically coupled to an air intake port 216A/216B and is configured to convert oxygen from incoming air into ozone. The ozone generators 206 may be powered by a power source 212 (e.g., a 120V/240V power supply). A power signal from power source 212 may be transformed via a transformer suitable for applying the voltage to the dielectric within the corona discharge tube of the ozone generator 206. For example, a transformer may be coupled to or integrated within a controller 208 for the ozone generator 206. In some embodiments, each controller 208 is simply a transformer.

In some embodiments, the ozone generators 206 may be operated at 110 volts/60 Hz and have an operating frequency of about 450 kHz and 550 kHz, with a power rating of less than about 15 watts, and with a unit performance for electrical consumption of about 32 watts. For example, the ozone generators 206 may have an operating frequency of about 480 kHz. Further, the ozone generators 206 can be provided according to ISO 9001 CE standards.

Each of the ozone generators 206 may be configured to produce from about 800 mg ozone per hour to about 1200 mg ozone per hour, although other ranges may be appropriate depending on the application. In some embodiments, each of the ozone generators 206 produces about 1000 mg ozone per hour. The ozone generators 206 may include other methods and systems for generating ozone, including but not limited to, electrochemical cells configured to generate ozone from water by placing an anode and a cathode in contact with opposite sides of a proton exchange membrane (PEM), and supplying power to the cell, whereby water flowing over the surface of the anode breaks down into hydrogen atoms and oxygen atoms that assemble to form $O_3$ (ozone).

The ozone supply unit 200 may further include an air dryer 214 (or filter), which may be externally coupled to the supply unit enclosure 202. The air dryer 214 is configured to remove moisture from air before the air is supplied to the ozone generators 206 through the one or more air intake ports 216. The air dryer 214 may be configured to dry the air to a minus dew point by removing water vapor or moisture therefrom, where the water could inhibit the production of ozone by the ozone generators 206.

In some embodiments, the air dryer 214 includes or is coupled to an air compressor. The pressure provided by the compressor can vary, where the pressure applied by the compressor can be balanced based on the flow rate of air received by the ozone generators 206 via the one or more air intake ports 216. For example, the compressor may be configured to compress the filtered air at least about 15 KPa (e.g., more particularly at a pressure of 18 KPa or about 2.6 psi) to provide a gas throughput in each ozone generator 206 of about 8 SCFH (standard cubic feet per hour). At these pressures, each ozone generator 206 has a residence time of the gas of about three seconds. The pressure applied by the compressor can affect the rate at which the gas flows through an ozone generator 206, which can affect contact time of the air with the components of the ozone generator 206, which can also affect mass gas transfer rates within the ozone generator 206.

The HVAC decontamination system 100 may further include at least one oxygen concentrator 102 configured to supply oxygen-enriched air to the one or more air intake ports 216 of the ozone supply unit 200. In embodiments, an oxygen concentrator 102 may be configured to direct the oxygen-enriched air through the air dryer 214. The oxygen concentrator 102 may also remove moisture from the air. In this regard, the incoming air may undergo two drying stages. The oxygen concentrator 102 may be fluidically coupled to the ozone supply unit 200 (e.g., to the air dryer 214 and/or air intake ports 216) by one or more tubes 104 (e.g., flexible tubing, pipes, etc.) for transferring oxygen-enriched air from the oxygen concentrator 102 to the ozone supply unit 200.

In embodiments, the ozone supply unit 200 includes a plurality of ozone generators 206. For example, in an embodiment illustrated FIG. 2, the ozone supply unit 200 includes two ozone generators 206. Each ozone generator 206 may be coupled to a respective air intake port 216 and ozone output port 220. However, in some embodiments, two or more ozone generators 206 may be fluidically connected in parallel between an air intake port 216 and an ozone output port 220. For example, splitters/combiners can be used to fluidically couple each pair/set of ozone generators 206 in parallel. The ozone supply unit 200 may additionally/alternatively include two or more ozone generators 206 connected in series with one other. Such configurations provide one or more backup ozone generators 206 in case of malfunction or inoperability of one or more of the other ozone generators 206. On average, each ozone generator 206 may have an operating life of about 10,000 working hours.

In some embodiments, the supply unit enclosure 202 also includes a vent 218 (e.g., an exhaust vent) to bring cool air into the supply unit enclosure 202 and/or remove hot air from the supply unit enclosure 202. The vent 218 may be equipped with a fan to further facilitate airflow.

As shown in FIG. 3, the ozone supply unit 200 may further include a relay 210 disposed within or otherwise coupled to the supply unit enclosure 202. The relay 210 may be configured to distribute incoming signals (e.g., power, communication, and/or control signals) to the one or more controllers 208. The relay 210 may include one or more switches or switchboards configured to transmit and receive signals via physical connectors (e.g., wires, cables, optical fibers, etc.). In some embodiments, the relay 210 may further include and/or may be coupled with one or more wireless communication interfaces (e.g., wireless receivers, transmitters, and/or transceivers) for sending signals from one device to the other.

The air analyzer 106 may be communicatively coupled to the ozone supply unit 200 via one or more connectors 112 (e.g., wires, cables, optical fibers, etc.) for transmitting signals between the ozone supply unit 200 and the air analyzer 106. For example, the one or more connectors 112 may communicatively couple the air analyzer 106 with the one or more controllers 206 of the ozone supply unit 200 via the relay 210. In other embodiments, the ozone supply unit 200 and the air analyzer 106 may include wireless communication interfaces (e.g., wireless receivers, transmitters, and/or transceivers) for sending signals from one device to the other.

In embodiments, the air analyzer 106 is an ozone gas monitor, such as the GasSens Ozone Gas Monitor or the A14/A11 Modular Gas Detector, manufactured by Analytical Technology, Inc. The air analyzer 106 is configured to monitor an amount of ozone per unit volume of air using an ozone sensor 108 disposed at a selected location within an air-conditioned environment (e.g., at or near a supply vent 124 or a blower output). In embodiments, the ozone sensor 108 is an ozone gas sensor/transmitter, such as the A14/A11 Ozone ($O_3$) Gas Sensor/Transmitter, manufactured by Analytical Technology, Inc. The air analyzer 106 is configured to receive sensor measurements from the ozone sensor 108 regarding the amount of ozone per unit volume of air at the selected location. For example, the ozone sensor 108 may be communicatively coupled to the air analyzer 106 via one or more connectors 110 (e.g., wires, cables, optical fibers, etc.) for transmitting signals between the ozone sensor 108 and the air analyzer 106. In other embodiments, the ozone sensor 108 and the air analyzer 106 may include wireless communication interfaces (e.g., wireless receivers, transmitters, and/or transceivers) for sending signals from one device to the other.

The air analyzer 106 can be programmed (e.g., via dip switches or any other user interface) to output one or more control signals when the amount of ozone per unit volume of air exceeds a predetermined threshold. The predetermined threshold or "setpoint" can be determined based on an air quality assessment of a treated environment (i.e., the air-conditioned environment in which the HVAC decontamination system 100 is employed). For occupant safety, it is preferred that the setpoint be as close as possible to the minimum ozone concentration necessary for reducing unpleasant odors and sufficiently disinfecting the treated environment. In embodiments, the setpoint may be in the range of 0.01 to 0.3 ppm, or more particularly in the range of 0.05 to 0.2 ppm for certain applications. At higher concentrations, it may be necessary to control a length of time that humans/animals are exposed and/or type of activity taking place in the ozone-enriched environment. For example, OSHA guidelines for ozone in the workplace are as follows: 0.2 ppm for no more than 2 hours exposure; 0.1 ppm for 8 hours per day exposure doing light work; 0.08 ppm for 8 hours per day exposure doing moderate work; and 0.05 ppm for 8 hours per day exposure doing heavy work.

The air analyzer 106 may be configured for continuous or intermittent monitoring. For example, the air analyzer 106 may be configured to collect sensor data (e.g., ozone measurements) from the ozone sensor 108 continuously or practically continuously (e.g., x samples/second, where x is an integer) or periodically (e.g., at n second, n minute, or n hour intervals, where n is an integer).

In embodiments, the air analyzer 106 is configured to transmit one or more control signals (based on the detected amount of ozone per unit volume of air) to the one or more controllers 208 of the ozone supply unit 200. The one or more controllers 208 are configured to: (i) cause the plurality of ozone generators 206 to generate ozone when the amount of ozone per unit volume of air is less than a predetermined threshold; and (ii) cause the plurality of ozone generators 206 to cease to generate ozone when the amount of ozone per unit volume of air exceeds the predetermined threshold. This may be accomplished in a number of ways. For example, in some embodiments, the air analyzer 106 is configured to generate one or more (ON or RUN) control signals for the one or more controllers 208 to cause the plurality of ozone generators 206 to generate ozone when the air analyzer 106 detects an amount of ozone per unit volume of air that is less than the predetermined threshold. In such embodiments, the air analyzer 106 may be configured to generate one or more (OFF or STOP) control signals for the one or more controllers 208 to cause the plurality of ozone generators 206 to stop generating ozone (e.g., by deactivating or shutting down) when the air analyzer 106 detects an amount of ozone per unit volume of air that is less than the predetermined threshold. In other embodiments, the air analyzer 106 is only configured to generate: (i) one or more (ON or RUN) control signals for the one or more controllers 208 to cause the plurality of ozone generators 206 to generate ozone when the air analyzer 106 detects an amount of ozone per unit volume of air that is less than the predetermined threshold; or (ii) one or more (OFF or STOP) control signals for the one or more controllers 208 to cause the plurality of ozone generators 206 to stop generating ozone (e.g., by deactivating or shutting down) when the air analyzer 106 detects an amount of ozone per unit volume of air that is less than the predetermined threshold. In such embodiments, the one or more controllers 208 are by default: (i) configured to run the ozone generators 206 only in response to the one or more (ON or RUN) control signals from the air analyzer 106; or (ii) configured to run the ozone generators 206 unless one or more (OFF or STOP) control signals are received from the air analyzer 106.

The one or more control signals may include instructions and/or power signals for the one or more controllers 208. Alternatively, the one or more control signals may simply include one or more status indicators (at setpoint, below setpoint, above setpoint, etc.) that cause the one or more controllers 208 to run or stop running the ozone generators 206. In simple implementations, the one or more control signals include a binary (e.g., "1" or "0") signal or "high" or "low" voltage signal that turns on/off the ozone generators 206 via the relay 210 and the one or more controllers/transformers 208.

As shown in FIG. 3, the ozone produced by the ozone generators 206 may flow through the ozone output ports 220 to one or more ozone supply tubes 114 (e.g., flexible tubing, pipes, etc.). The ozone output ports 220 and/or ozone supply tubes 114 may be configured to output the ozone directly into the treated environment, into a diffuser/fan, or any mechanism for spreading the ozone within the treated environment to reduce odors and/or disinfect air circulating through the environment. As shown in FIG. 1, certain embodiments of the HVAC decontamination system 100 are configured to output ozone into an air-conditioned environment via the HVAC system. This helps distribute the ozone more evenly within the treated environment (i.e., the air-conditioned environment) and can also serve an additional function of disinfecting or otherwise cleansing the ductwork of the HVAC system.

In the embodiment illustrated in FIG. 1, the one or more ozone supply tubes 114 are configured to deliver the ozone generated by the ozone generators 206 to an air return duct 116 of a HVAC system. The one or more ozone supply tubes 114 are configured to release the ozone near an air return vent or directly within the air return duct 116. In some embodiments, the HVAC decontamination system 100 includes an air diffuser 118 (e.g., sometimes referred to as an "air knife" or "air spreader") between the one or more ozone supply tubes 114 and the air return duct 116. The air diffuser 118 may be configured to diffuse or spread the ozone into the air return duct 116 to help mix the ozone with the air flowing through the air return duct 116.

The ozone (with the return air) may then flow through the air return duct 116 into an air handler 120 that is configured to condition the air received via the air return duct 116. For example, the air handler 120 may circulate the air within one or more chambers or ducts that include heating or cooling elements and/or a separate supply of hot/cold air. The air handler 120 may help to evenly mix/diffuse the ozone into the air by circulating and/or blowing the air within the one or more chambers or ducts.

The air handler 120 may be configured to output the conditioned air (containing ozone) into a supply duct 122 that delivers conditioned air from the air handler to one or more supply vents 124 (e.g., supply vents 124A, 124B, 124C, 124D, etc.). The one or more supply vents 124 are configured to output the conditioned air (containing ozone) into the air-conditioned environment.

In embodiments, the ozone sensor 108 may be positioned near a supply vent 124 (e.g., supply vent 124A) so that the air analyzer 106 can monitor the ozone concentration of the air coming out of the HVAC system. For example, the ozone sensor 108 may be located within 25 feet of a supply vent 124 of the HVAC system, e.g., within a range of 0.1 to 25 feet, or more particularly within a range of 0.1 to 10 feet or 0.1 to 5 feet for certain applications. In some embodiments, the ozone sensor 108 may be attached to a supply vent 124 or located within a supply duct 122. Alternatively, the ozone sensor 108 may be positioned near a return vent so that the air analyzer 106 can monitor the ozone concentration of the air going back into the HVAC system. For example, the ozone sensor 108 may be located within 25 feet of a return vent of the HVAC system, e.g., within a range of 0.1 to 25 feet, or more particularly within a range of 0.1 to 10 feet or 0.1 to 5 feet for certain applications. In some embodiments, the ozone sensor 108 may be attached to a return vent or located within an air return duct 116.

By maintaining the ozone concentration of conditioned air output through supply vents 124 or suctioned through return vents at a setpoint or within a range of lower and upper concentration limits, the HVAC decontamination system 100 helps ensure sufficient ozone levels in the treated environment to reduce odors and/or disinfect the air, while also making sure to avoid unsafe levels of ozone that could potentially harm humans/animals in the treated environment. However, in some implementations, the ozone sensor 108 may not need to be placed in proximity of a supply vent, return vent, or HVAC ductwork to monitor air quality. While monitoring air going into or out of the HVAC system may be preferred, the ozone sensor 108 may be located virtually anywhere within an environment as long as the ozone sensor 108 is capable of detecting a representative sample of air circulating within the environment.

Although FIGS. 1 through 3 illustrate one ozone supply unit 200 and one air analyzer 106, it is understood that there may be any number of identically or similarly structured ozone supply units 200 and/or air analyzers 106 in the HVAC decontamination system 100 for redundancy, different zones, and/or output requirements. In this regard, any components or configurations described with regard to the ozone supply unit 200 and/or air analyzer 106 in FIGS. 1 through 3 are applicable to any number of the ozone supply units 200 and/or air analyzers 106 in the HVAC decontamination system 100.

Although the invention has been described with reference to embodiments illustrated in the attached drawings, equivalents or substitutions may be employed without departing from the scope of the invention as recited in the claims. Components illustrated and described herein are examples of devices and components that may be used to implement embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. A HVAC decontamination system with regulated ozone output based on monitored ozone level in ambient air, the HVAC decontamination system comprising:
   an ozone supply unit comprising:
     a supply unit enclosure having one or more air intake ports and one or more ozone output ports;
     a plurality of ozone generators disposed within the supply unit enclosure, the plurality of ozone generators being fluidically coupled to the one or more air intake ports and the one or more ozone output ports of the supply unit enclosure; and
     one or more controllers disposed within the supply unit enclosure, the one or more controllers being communicatively coupled to the plurality of ozone generators;
   an air analyzer configured to monitor an amount of ozone per unit volume of air using an ozone sensor disposed at a selected location, the air analyzer being configured to transmit one or more control signals to the one or more controllers of the ozone supply unit when the amount of ozone per unit volume of air exceeds a predetermined threshold, the one or more controllers being configured to cause the plurality of ozone generators to generate ozone when the amount of ozone per unit volume of air is less than the predetermined threshold and being further configured to cause the plurality of ozone generators to cease to generate ozone in response to the one or more control signals; and
   one or more tubes coupled to the one or more ozone output ports of the supply unit enclosure, the one or more tubes being configured to deliver the ozone generated by the plurality of ozone generators to an air return duct of a HVAC system.

2. The HVAC decontamination system of claim 1, wherein the one or more controllers comprise a plurality of controllers, wherein each of the controllers is communicatively coupled to a respective ozone generator of the plurality of ozone generators.

3. The HVAC decontamination system of claim 1, further comprising:
   an air diffuser between the one or more tubes and the air return duct, the air diffuser being configured to diffuse the ozone into the air return duct.

4. The HVAC decontamination system of claim 3, wherein the ozone sensor is located within 25 feet of a supply vent of the HVAC system.

5. The HVAC decontamination system of claim 1, further comprising:
   one or more oxygen concentrators configured to supply oxygen-enriched air to the one or more air intake ports of the ozone supply unit.

6. The HVAC decontamination system of claim 5, wherein the ozone supply unit further comprises an air dryer externally coupled to the supply unit enclosure, the air dryer being configured to remove moisture from the oxygen-enriched air before the oxygen-enriched air is supplied to the plurality of ozone generators through the one or more air intake ports.

7. A HVAC decontamination system with regulated ozone output based on monitored ozone level in ambient air, the HVAC decontamination system comprising:
   an ozone supply unit comprising:
     a supply unit enclosure having one or more air intake ports and one or more ozone output ports;
     a plurality of ozone generators disposed within the supply unit enclosure, the plurality of ozone generators being fluidically coupled to the one or more air intake ports and the one or more ozone output ports of the supply unit enclosure; and
     one or more controllers disposed within the supply unit enclosure, the one or more controllers being communicatively coupled to the plurality of ozone generators;

an air analyzer configured to monitor an amount of ozone per unit volume of air using an ozone sensor disposed at a selected location, the air analyzer being configured to transmit one or more control signals to the one or more controllers of the ozone supply unit when the amount of ozone per unit volume of air is below a predetermined threshold, the one or more controllers being configured to cause the plurality of ozone generators to generate ozone in response to the one or more control signals; and one or more tubes coupled to the one or more ozone output ports of the supply unit enclosure, the one or more tubes being configured to deliver the ozone generated by the plurality of ozone generators to an air return duct of a HVAC system.

8. The HVAC decontamination system of claim 7, wherein the one or more controllers comprise a plurality of controllers, wherein each of the controllers is communicatively coupled to a respective ozone generator of the plurality of ozone generators.

9. The HVAC decontamination system of claim 7, further comprising:

an air diffuser between the one or more tubes and the air return duct, the air diffuser being configured to diffuse the ozone into the air return duct.

10. The HVAC decontamination system of claim 9, wherein the ozone sensor is located within 25 feet of a supply vent of the HVAC system.

11. The HVAC decontamination system of claim 7, further comprising:

one or more oxygen concentrators configured to supply oxygen-enriched air to the one or more air intake ports of the ozone supply unit.

12. The HVAC decontamination system of claim 11, wherein the ozone supply unit further comprises an air dryer externally coupled to the supply unit enclosure, the air dryer being configured to remove moisture from the oxygen-enriched air before the oxygen-enriched air is supplied to the plurality of ozone generators through the one or more air intake ports.

13. A HVAC system, comprising:

an air return duct;

an air handler configured to condition air received via the air return duct;

a supply duct configured to deliver conditioned air from the air handler to one or more supply vents that are configured to output the conditioned air;

an ozone supply unit comprising:

a supply unit enclosure having one or more air intake ports and one or more ozone output ports;

a plurality of ozone generators disposed within the supply unit enclosure, the plurality of ozone generators being fluidically coupled to the one or more air intake ports and the one or more ozone output ports of the supply unit enclosure; and one or more controllers disposed within the supply unit enclosure, the one or more controllers being communicatively coupled to the plurality of ozone generators;

an air analyzer configured to monitor an amount of ozone per unit volume of air using an ozone sensor configured to sense the conditioned air output by the one or more supply vents, the air analyzer being configured to transmit one or more control signals based on the amount of ozone per unit volume of air to the one or more controllers of the ozone supply unit, the one or more controllers being configured to cause the plurality of ozone generators to generate ozone when the amount of ozone per unit volume of air is less than a predetermined threshold and being further configured to cause the plurality of ozone generators to cease to generate ozone when the amount of ozone per unit volume of air exceeds the predetermined threshold; and one or more tubes coupled to the one or more ozone output ports of the supply unit enclosure, the one or more tubes being configured to deliver the ozone generated by the plurality of ozone generators to the air return duct.

14. The HVAC system of claim 13, wherein the one or more controllers comprise a plurality of controllers, wherein each of the controllers is communicatively coupled to a respective ozone generator of the plurality of ozone generators.

15. The HVAC system of claim 13, further comprising:

an air diffuser between the one or more tubes and the air return duct, the air diffuser being configured to diffuse the ozone into the air return duct.

16. The HVAC system of claim 13, wherein the ozone sensor is located within 25 feet of the one or more supply vents.

17. The HVAC system of claim 13, further comprising:

one or more oxygen concentrators configured to supply oxygen-enriched air to the one or more air intake ports of the ozone supply unit.

18. The HVAC system of claim 17, wherein the ozone supply unit further comprises an air dryer externally coupled to the supply unit enclosure, the air dryer being configured to remove moisture from the oxygen-enriched air before the oxygen-enriched air is supplied to the plurality of ozone generators through the one or more air intake ports.

* * * * *